United States Patent [19]

Salzburg et al.

[11] Patent Number: 5,723,098
[45] Date of Patent: Mar. 3, 1998

[54] PROCESS FOR THE RECOVERY OF CATALYSTS IN ADIPIC ACID PRODUCTION

[76] Inventors: Herbert Salzburg, Fasanenstr. 11, 42799 Leichlingen; Georg Steinhoff, Schönwasserstr.214c, 47800 Krefeld; Heiko Hoffmann, Heitberg 6, 51427 Bergisch Gladbach; Helmut Kaponig, Blockstr.20, 46049 Oberhausen, all of Germany

[21] Appl. No.: 706,473

[22] Filed: Sep. 4, 1996

[30] Foreign Application Priority Data

Sep. 12, 1995 [DE] Germany .......... 195 33 688.7

[51] Int. Cl.$^6$ .......... C07C 55/00; C02F 1/42; C01G 49/00
[52] U.S. Cl. .......... 423/139; 210/670; 210/688; 423/24; 423/63; 562/590
[58] Field of Search .......... 423/24, 63, 139; 562/590; 210/688, 670

[56] References Cited

U.S. PATENT DOCUMENTS

| | | | |
|---|---|---|---|
| 2,858,335 | 10/1958 | Hill et al. | 260/537 |
| 2,897,050 | 7/1959 | Jaffe | 210/688 |
| 3,240,556 | 3/1966 | Bhappu | 210/688 |
| 3,554,692 | 1/1971 | Brast et al. | 23/22 |
| 3,965,164 | 6/1976 | Blay | 260/531 R |
| 3,983,208 | 9/1976 | Blay | 562/590 |
| 4,375,552 | 3/1983 | Kuceski | 562/590 |
| 5,182,251 | 1/1993 | Bruening et al. | 502/401 |
| 5,210,297 | 5/1993 | Frank et al. | 562/593 |
| 5,449,462 | 9/1995 | Horwitz et al. | 210/688 |

*Primary Examiner*—Wayne Langel
*Attorney, Agent, or Firm*—Joseph C. Gil; Richard E. L. Henderson

[57] ABSTRACT

The invention relates to a process for the selective recovery of catalysts used in the production of adipic acid by (a) separating adipic acid from the reaction solution, (b) exposing the resultant reaction solution to a sulfonated ion exchanger, thereby binding iron, copper, and vanadium ions to said sulfonated ion exchanger, (c) separating the ion-exchanger from the reaction solution, (d) washing the separated ion exchanger with nitric acid to obtain an acid eluate, and (e) exposing the acid eluate to an ion exchanger modified with aminophosphonic acid groups, thereby removing the iron ions from the acid eluate.

1 Claim, No Drawings

PROCESS FOR THE RECOVERY OF CATALYSTS IN ADIPIC ACID PRODUCTION

BACKGROUND OF THE INVENTION

The invention relates to a process for the recovery of catalysts used in adipic acid production.

Adipic acid is produced industrially, for example, by catalytic oxidation of cyclohexanol. Copper and vanadium salts can be used as catalysts and concentrated nitric acid can be used as oxidant.

The reaction solution of catalyst and oxidant becomes enriched with iron ions by extraction of iron from the reaction vessels. This iron content can interfere with or even prevent the further use of the reaction solution.

Processes in which the metals of the process solution can be extracted with ion exchangers are known. Such extraction processes usually occur during work-up of the by-products (i.e., glutaric acid and succinic acid) from the adipic acid synthesis. U.S. Pat. No. 3,965,164 describes the treatment of the whole mixture of metals and dicarboxylic acids with process waste gas (i.e., $NO_x$ and $N_2O$) whereby vanadium is concentrated during the regeneration of the ion exchanger.

European Patent Application 494,416 describes the decomposition of the metal nitrates, for example, by thermal treatment. As a result, iron was not removed by the ion exchanger, although vanadium and copper may have been removed by cation exchange.

A further possible separation of copper and vanadium on the one hand and iron on the other hand involves pre-rinsing with weak nitric acid during the regeneration of the ion exchanger in order to elute Cu and V preferentially, followed by washing out the iron (as well as residues of Cu and V) with stronger $HNO_3$.

In another method, described in U.S. Pat. No. 3,554,692, copper and vanadium are selectively washed out of the ion exchanger with $HNO_3$ (pH 1.8 to −0.3), whereas the iron is eluted as a phosphate complex.

In the selective regeneration of the ion exchanger by dilute acids it is disadvantageous to expend the necessarily large amounts of the acid used in regeneration. When using auxiliary chemicals it is disadvantageous to supply a "foreign" substance to the oxidation process during catalyst re-use, thereby necessitating purification of the copper and vanadium compounds before re-use. Furthermore, because iron concentrations are generally considerably smaller than copper and vanadium concentrations, the probability of the preferred iron exchange is already greatly impaired.

Another disadvantage of such processes is that a more or less greater disappearance of iron during the selective regeneration must be accepted if excessive loss of copper and vanadium is to be avoided.

A process has now been found by which iron ions that arise, for example, by extraction from the reaction vessels can be removed from reaction solutions used for the oxidation of cyclohexanol to adipic acid with concentrated nitric acid in the presence of iron and vanadium salts as catalysts.

SUMMARY OF THE INVENTION

The invention relates to a process for the selective removal of iron ions from reaction solutions formed during nitric acid oxidation of cyclohexanol to adipic acid using concentrated nitric acid in the presence of copper and/or vanadium salts comprising (a) separating adipic acid from the reaction solution, (b) exposing the resultant reaction solution to a sulfonated ion exchanger, thereby binding iron, copper, and vanadium ions to said sulfonated ion exchanger, (c) separating the ion-exchanger from the reaction solution, (d) washing the separated ion exchanger with nitric acid to obtain an acid eluate, and (e) exposing the acid eluate to an ion exchanger modified with aminophosphonic acid groups, thereby selectively removing the iron ions from the acid eluate.

DETAILED DESCRIPTION OF THE INVENTION

For removal according to the invention of all metal ions from the reaction solution obtained during adipic acid production, the acidic reaction solution from which adipic acid has been removed is passed over a sulfonated ion exchanger, preferably a sulfonated polystyrene ion exchanger such as a LEWATIT® ion exchanger. The ion exchanger is then separated from the reaction solution (for example, by filtration, centrifugation, decantation, and the like) and regenerated with nitric acid, the metal ions being washed out (i.e., eluted) and the ion exchanger regenerated. The eluate is then passed over an ion exchanger (e.g., a polystyrene resin) that is modified with aminophosphonic acid groups, preferably alkylaminophosphonic acid groups such as methylammonium phosphonic acid groups. During this process the iron ions are removed selectively and almost quantitatively from the eluate and the copper and vanadium ions remain in solution. This copper- and vanadium-containing solution can be reused directly for the oxidative production of adipic acid.

The process according to the invention can be carried out either continuously or discontinuously.

When carrying out the process according to the invention, all metals are first removed from the reaction mixture with a cation exchanger, such as LEWATIT® SP 112, preferably at a point in the adipic acid recovery process at which the concentration of nitric acid is below 10%. The metal-containing regenerate obtained by regenerating the ion exchanger with nitric acid (preferably 20 to 30% nitric acid) is subsequently passed at the given acidic conditions over an ion exchanger containing alkylaminophosphonic acid groups. At first, even copper and vanadium are absorbed but subsequently the iron, despite its concentration being powers of ten lower, displaces the copper and vanadium.

Both ion-exchange steps can be carried out between 5° C. and 100° C., preferably between 40° C. and 75° C.

Preferably, the vessel containing the acid used to regenerate the sulfonated ion exchanger is provided with a recycling circuit in which the iron is removed by pumping the acid eluate through the ion exchanger containing aminophosphonic acid groups. The regenerating acid, which is thus deprived of iron, can be used many times for the regeneration of the first ion exchanger. Because fresh acid (i.e., 20 to 30% $HNO_3$) is used for rinsing, the pH can easily be adjusted between 0 and −1.5.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all parts and percentages are parts by weight and percentages by weight, respectively.

EXAMPLES

The regenerating acids used in the examples contain metals, for example, in the following concentrations:
Copper (Cu) 5–35 g/l (preferably 10–28 g/l)
Vanadium (V) 0.5–10 g/l (preferably 1–6 g/l)
Iron (Fe) 0.02–2.5 g/l (preferably 0.040–0.250 g/l)

If the capacity of the methylaminophosphonic acid ion-exchanger resin is exhausted, the solution remaining in the resin bed can be rinsed with one bed volume ("BV") of fresh acid (6 to 31.5% N $HNO_3$, preferably 9 to 16% $HNO_3$), so that the loss of catalyst metal is avoided. The ion exchanger can be regenerated with 5 to 50% phosphoric acid.

Example 1

At a loading rate of about 10 BV/h, 300 ml of LEWATIT® SP 112 were loaded (T=50° C.) with about 6 BV of a solution containing 6 g/l Cu, 1.66 g/l V, and 68 mg/l Fe. The eluate contained less than 10 mg/l Cu, less than 10 mg/l V, and less than 20 mg/l Fe.

The ion exchanger was regenerated with 3N $HNO_3$ using 3 BV of $HNO_3$ and 1 BV of $H_2O$. The regenerating acid contained 11.21 g/l Cu, 0.82 g/l V, and 42 mg/l Fe.

The regenerating acid was circulated at a rate of 600 ml/h for 3 hours through a column containing 100 ml of polystyrene resin modified with methylaminophosphonic acid (ion exchanger). 100 ml of 3N $HNO_3$ were subsequently used for rinsing. The eluate contained 8.4 g/l Cu, 62 mg/l V, and less than 1 mg/l Fe.

Example 2

500 ml of regenerating acid, prepared as in Example 1, was stirred with 15 ml of methylaminophosphonic acid exchanger resin at room temperature.

Metal Concentrations

|  | Cu | V | Fe |
| --- | --- | --- | --- |
| Starting solution | 16 g/l | 4.1 g/l | 320 mg/l |
| Final concentration after 10 h | 16 g/l | 4.0 g/l | <23 mg/l |

Example 3

One liter of regenerating acid, prepared as in Example 1, was stirred with 40 ml of methylaminophosphonic acid resin at room temperature for 48 h.

Metal Concentrations

|  | Cu | V | Fe |
| --- | --- | --- | --- |
| Starting concentration | 28 g/l | 15.0 g/l | 610 mg/l |
| Final concentration | 27 g/l | 13.0 g/l | 33 mg/l |

Example 4

A regenerating acid, prepared as in Example 1, was enriched with $Cu(NO_3)_2$, $V_2O_5$ and $Fe(NO_3)_3.H_2O$ in such a way that a starting metal concentration of 28 g/l Cu, 15 g/l V, and 610 mg/l Fe was produced. This solution was stirred for 48 hours with 20 ml of methylaminophosphonic acid resin. Final concentration of the solution was 27 g/l Cu, 13 g/l V, and 33 mg/l Fe.

Example 5

250 ml of regenerating acid, prepared as in Example 1, was pumped through 74 ml of methylaminophosphonic acid resin.

Metal Concentrations

|  | Cu | V | Fe |
| --- | --- | --- | --- |
| Starting concentration | 10 g/l | 2.5 g/l | 1.5 g/l |
| Final concentration after about 36 h | 10 g/l | 2.2 g/l | 55 mg/l |

Example 6

One liter of regenerating acid (pH −1.6) was stirred with 105 ml of methylaminophosphonic acid resin at room temperature.

Metal Concentrations

|  | Cu | V | Fe |
| --- | --- | --- | --- |
| Starting concentration | 15 g/l | 3.6 g/l | 2.3 g/l |
| Final concentration after about 24 h | 15 g/l | 3.6 g/l | 180 mg/l |

Example 7

1.5 liter of regenerating acid, prepared as in Example 1, were pumped through 45 g of moist LEWATIT® VP OC 1060 exchanger resin. Metals in the starting solution: 13 g/l Cu (19.5 g Cu), 3.2 g/l V (4.8 g V), and 270 mg/l Fe (405 mg Fe)

1.44 liter of eluate was obtained, having the following absolute metal contents: 16.81 g Cu, 3.99 g V, and 4.7 mg Fe Intensive rinsing with 350 ml 1.5N $HNO_3$ yielded 2.8 g Cu, 0.825 g V, and 1.4 mg Fe.

What is claimed is:

1. A process for the selective removal of iron ions from reaction solutions formed during nitric acid oxidation of cyclohexanol to adipic acid using concentrated nitric acid in the presence of copper and/or vanadium salts comprising (a) separating adipic acid from the reaction solution, (b) exposing the resultant reaction solution to a sulfonated ion exchanger, thereby binding iron, ions and copper and/or vanadium ions to said sulfonated ion exchanger, (c) separating the ion-exchanger from the reaction solution, (d) washing the separated ion exchanger with nitric acid to obtain an acid eluate, and (e) exposing the acid eluate to an ion exchanger modified with aminophosphonic acid groups, thereby removing the iron ions from the acid eluate.

* * * * *